United States Patent [19]
Mohapatra et al.

[11] Patent Number: 5,525,905
[45] Date of Patent: Jun. 11, 1996

[54] PATIENT HANDLING SYSTEM FOR USE ON MULTIPLE IMAGING SYSTEMS

[75] Inventors: Surya N. Mohapatra, Chesterland; Paul M. Margosian, Lakewood; Fredrick F. Awig, Lyndhurst, all of Ohio

[73] Assignee: Picker International, Inc., Cleveland, Ohio

[21] Appl. No.: 342,584

[22] Filed: Nov. 21, 1994

[51] Int. Cl.⁶ ..................................................... G01V 3/00
[52] U.S. Cl. ........................................ 324/318; 128/653.5
[58] Field of Search .................................... 324/318, 322, 324/300, 307, 309; 128/653.5

[56] References Cited

U.S. PATENT DOCUMENTS

| | | | |
|---|---|---|---|
| 4,567,894 | 2/1986 | Bergman | 128/653.5 |
| 4,727,328 | 2/1988 | Carper et al. | 324/318 |
| 5,178,146 | 1/1993 | Giese | 128/653.5 |

OTHER PUBLICATIONS

Title: Industrial Design 25th Annual Design Review; (1979) Author: Edward K. Carpenter; pp.: 106 and 109.
Title: Synerview CT; Brochure of Picker Corporation; (Apr. 1979); pp.: 1–20.

Primary Examiner—Louis M. Arana
Attorney, Agent, or Firm—Timothy B. Gurin; John J. Fry

[57] ABSTRACT

A object handling system is moveable between various diagnostic imaging apparatus for imaging thereby. The handling system has an object handling computer 34 for storing object identification data and imaging data. Selectively linking the object handling computer 34 with a first imaging system provides the first imaging system with access to the object identification data and imaging data for use in the production of diagnostic images thereby. Similarly, the object identification data and imaging data are available to a second imaging system for use in the production of diagnostic images thereby when the object handling computer 34 is selectively linked thereto. The object identification data is associated with the diagnostic images produced by various imaging system for subsequent correlation of the object with the diagnostic images of the object. The object handling computer 34 also modifies various automated table movement apparatus as a function of the imaging system to which the handling system is selectively linked.

24 Claims, 5 Drawing Sheets

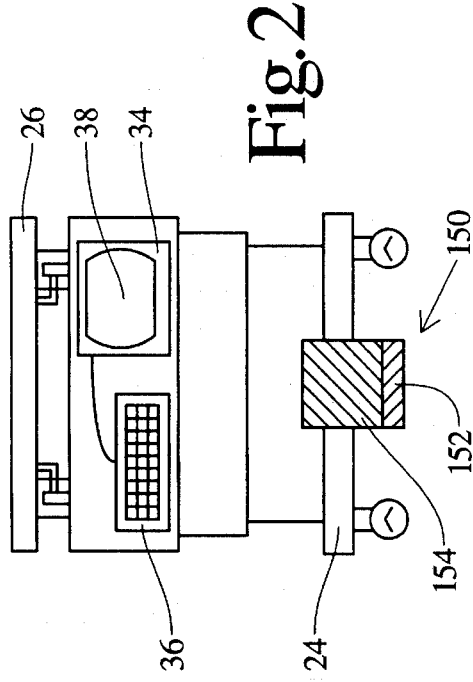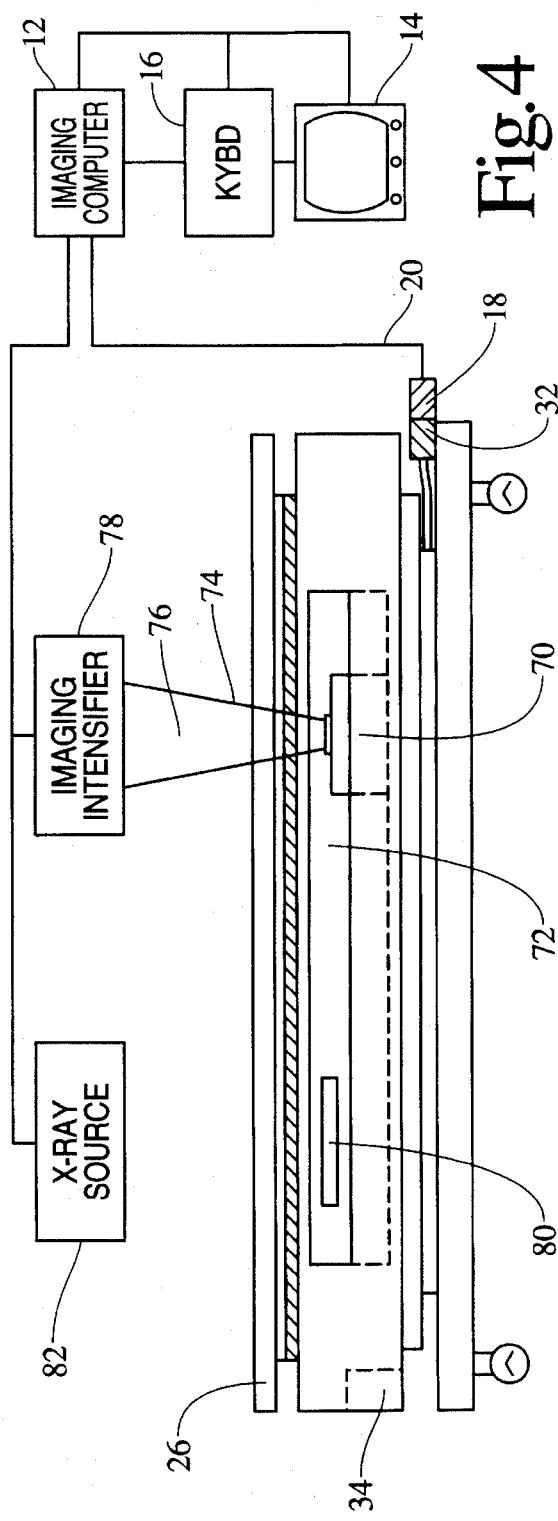

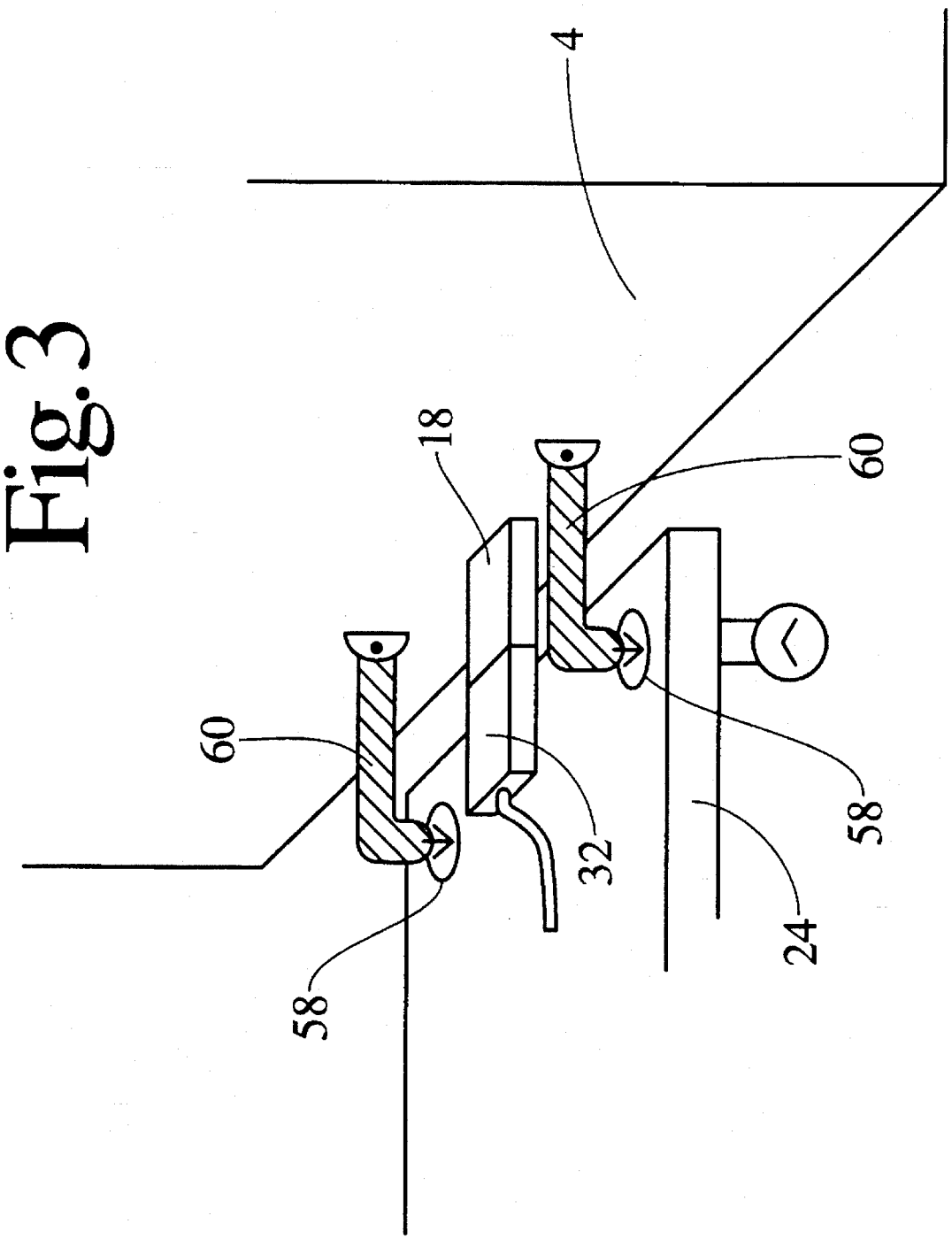

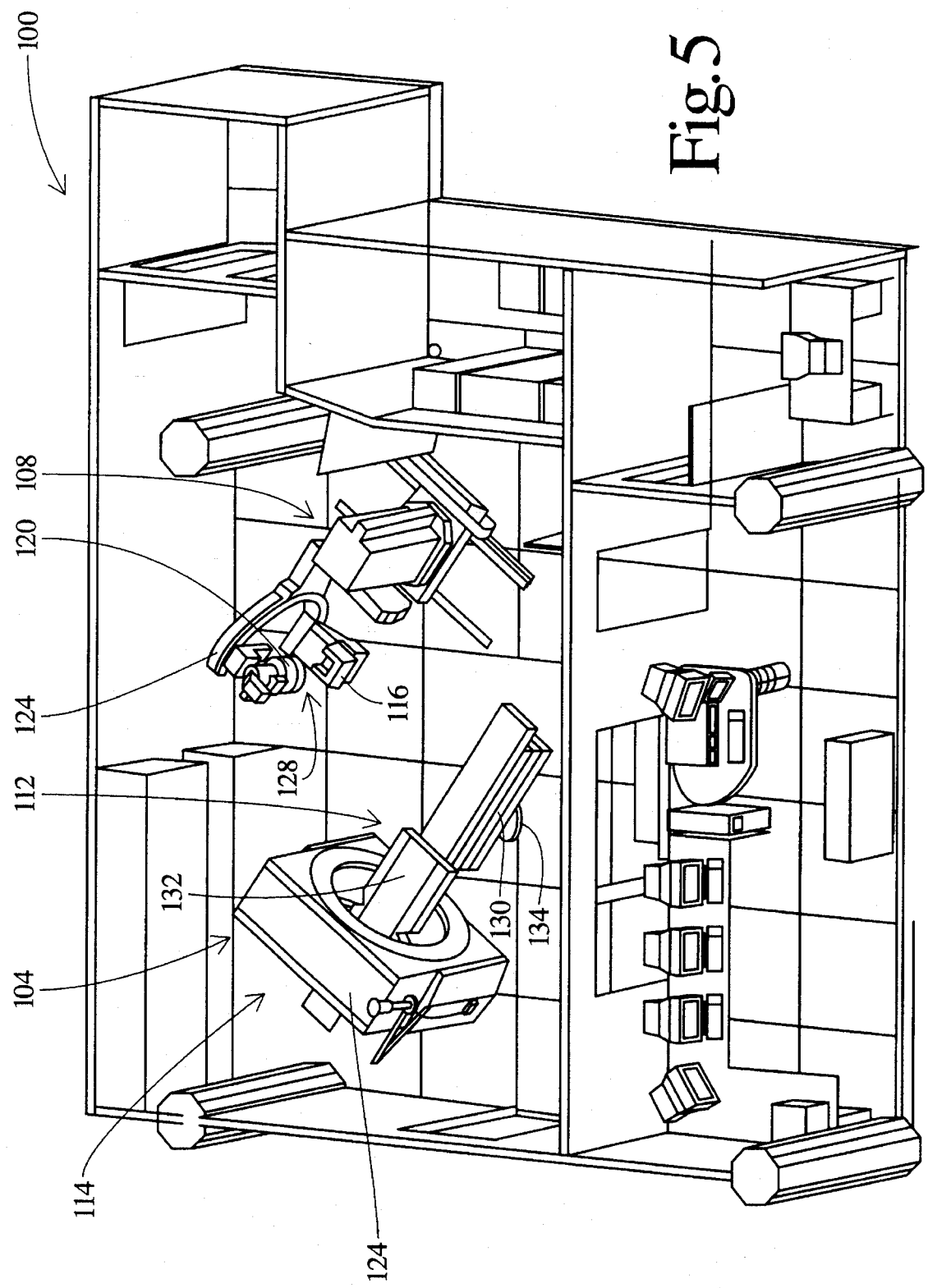

PATIENT HANDLING SYSTEM FOR USE ON MULTIPLE IMAGING SYSTEMS

BACKGROUND OF THE INVENTION

This invention relates to a moveable patient handling system for use in diagnostic medical imaging.

Heretofore, each modality of diagnostic medical imaging equipment, such as Computed Tomography (CT), X-ray, Nuclear Medicine and Magnetic Resonance Imaging (MRI), was equipped with a dedicated handling system for a patient or object under examination. These object handling systems generally included a table disposed over a base. The top side of the table is used to support an object, such as a patient, for imaging. The mechanical configuration of the imaging equipment to which each object handling system is mated often affects the configuration and features for each type of object handling system. For example, CT and MRI imaging equipment generally have gantries that form imaging spaces. These imaging spaces are generally horizontal to the floor and often have part of the gantry disposed between the imaging space and the floor. Because of the construction of these gantries, it is often necessary to dispose the base on the floor adjacent the gantry and extend the table relative to the base and into the imaging space. In contrast, with general purpose x-ray systems it is possible to have a configuration wherein there is no fixed gantry. Accordingly, the table and base can be disposed between the source of radiation and the floor and the table can remain over the base. Another imaging equipment feature that affects the object handling system configuration is the height of the imaging space from the floor. For example, if the height of an imaging space for a CT is different from the height of an imaging space for an MRI, the height of the object handling system associated with each system must be adjusted accordingly. The physics of a specific imaging modality configuration also affects, in part, the features of an object handling system. For example, tables designed for use exclusively in an MRI environment are made from fiberglass composites. Similarly, tables designed for use exclusively in radiation transmissive modalities, such as X-ray and CT, are preferably made from carbon composites. The selection of a fiberglass or carbon composite table is motivated, in part, by a desire to minimize the effect of the table on the imaging modality with which the table is being used. 2 With CT and MRI imaging equipment a table movement means, such as a motor, is often used to extend the table relative to the base and into the imaging space. In contrast, with object handling equipment used with X-ray and Nuclear Camera equipment the table often remains fixed over the base during imaging and the x-ray source and Nuclear Camera equipment are moved relative to the fixed table. Moreover, within a specific imaging modality, e.g., X-ray, more than one object handling system having different features is often available depending on the type of imaging to be performed and the desired object handling system features. For example, some object handling systems have a tilting feature that allows the table to be tiled from horizontal to vertical. Other object handling systems have a table that "floats" on the base thereby allowing the table to be moved in one or more directions in a horizontal plane. Still other tables may only have a top fixed at one position over the base.

A drawback to having a dedicated object handling system for different modalities of diagnostic imaging equipment or different imaging equipment of one modality is that the patient must be moved to each object handling system for imaging by the respective imaging equipment. Specifically, the patient is often disposed on a transportation gurney for movement into and out of an imaging room. Once in the room the patient is moved from the gurney to the object handling system to be imaged. After the imaging procedure is complete, the patient is returned to the gurney and transported out of the imaging room. One drawback to this arrangement is when the patient is being sequentially imaged on two or more diagnostic imaging apparatus, it is necessary to move the patient between the gurney and the object handling system and back again for each imaging equipment the patient encounters. Another drawback to this arrangement is that if the patient is unable to assist in moving between the gurney and object handling system, two or more medical personnel may be needed to move the patient each time resulting in inefficient use of such personnel whose time and talents may be more effectively used elsewhere. Still another drawback is that an object handling system is generally associated with a specific imaging equipment. Thus, if a feature of the object handling system is inoperative, such as the table movement means used to extend the table relative to the base and into the imaging space of a CT or MRI, the ability to use the imaging equipment is affected.

In some modalities of diagnostic medical imaging, the imaging equipment, e.g., CT and MRI, has one or more detectors for receiving imaging information from the patient. The received imaging information is converted to electrical signals by the detectors. These electrical signals are processed by an imaging computer and converted into viewable images of the patients anatomy. Data regarding the identification of the patient is often entered into the imaging computer, via a keyboard, for association of the viewable images with the patient identification data. By associating the viewable images with the patient identification data, subsequent correlation of the images with an appropriate patient can be made. This patient identification data may include, for example, name, sex, date-of-birth, social security number, insurance information, examination specific information, e.g., technique factor, slice number, and the like. Moving a patient from one imaging equipment to another requires this patient identification data to be entered into the computer of each imaging equipment so that a correlation between the patient being imaged and the resultant images is achieved. Drawbacks of having to enter patient data more than once is the time required to enter such data at each imaging equipment and the potential for operator entry error during multiple data entries. One way to overcome these drawbacks is to have a computer network connecting the various imaging equipment whereby the patient data can be entered once and retrieved at each imaging equipment. A drawback to the computer network, however, is that the patient being imaged must be accurately identified at each imaging equipment. If the patient is incorrectly identified, improper correlation between the patient and the resultant images can occur.

The present invention contemplates an improved object handling system that overcomes the above problems and others.

SUMMARY OF THE INVENTION

In accordance with one facet of the present invention a medical diagnostic imaging means for producing medical diagnostic images of an object is provided. The medical diagnostic imaging means includes a diagnostic imaging equipment of a first type for producing a first diagnostic image of the object and a diagnostic imaging equipment of a second type for producing a second diagnostic image of the object. The first and second imaging equipment have respective first and second imaging computers for controlling the production of diagnostic images thereby. The first and second imaging equipment form respective first and second imaging spaces. The medical diagnostic imaging means includes an object handling system. The object handling system has a table for supporting the object during examination, a base for supporting the table above a floor and a computer for storing data relating to the identification of the object under examination. A linking means is provided for selectively linking the object handling system computer to one of the first and second imaging equipment. The linking means provides a data communication path between the object handling system computer and the computer of the selected one of the first and second imaging equipment such that the identification data stored in the object handling computer is available to the computer of the selected one of the first and second imaging equipment for use in the production of diagnostic images.

In accordance with another aspect of the invention, a means for entering the identification data into the object handling system computer is provided.

In accordance with still another aspect of the invention, a base movement means is disposed between the base and the floor for allowing movement of the base and table from the selected one of the first and second imaging equipment to the other imaging equipment.

In accordance with still another aspect of the invention, the object handling system includes at least one of a means for disposing said table into the imaging space of the selected one of the first and second imaging systems and a means for adjusting the height of the table from the floor. A table lock for locking the table in a selected position relative to the base is also provided.

In accordance with still another aspect of the invention, one of the first and second imaging computers store positioning data relating to the relative position of the table and the respective imaging space necessary for object examination. The positioning data is available to the object handling system computer, via the data communication path, for use during the production of diagnostic images. The object handling system computer controls the at least one of the means for disposing and means for adjusting as a function of the positioning data.

In accordance with a more limited aspect of the invention, the linking means includes a means for securing the base relative to at least one of the first and second imaging spaces.

In accordance with still another more limited aspect of the invention, the linking means is comprised of a first connector connected to the computer of the selected one of the first and second imaging systems and a second connector connected to the object handling computer, said first and second connectors designed to mate together. Alternatively, the linking means is comprised of one of an r.f. link and an optical communications link operating in one of the infrared, visual or ultraviolet range.

In accordance with still another more limited aspect of the invention, the object handling system further includes at least one of a film carrier, an x-ray sensitive array and an image intensifier.

In accordance with another facet of the invention a medical diagnostic imaging room is provided. The imaging room includes a first diagnostic imaging equipment for producing a first diagnostic image of an object and a second diagnostic imaging equipment for producing a second diagnostic image of the object. The first and second imaging equipment form respective first and second imaging spaces. The imaging room also includes a means for sustaining an object during examination by the first and second diagnostic imaging equipment. The sustaining means includes a table for supporting the object and table support for supporting the table relative to the floor. The table support is moveable between the first and second imaging equipment such that said table is selectively disposable in the first and second imaging spaces.

In accordance with another aspect of the invention, a table movement means is disposed between the table and the support means for moving the table relative to the support means.

In accordance with yet another aspect of the invention, the sustaining means includes a computer connected to the table movement means. The sustaining means computer is selectively connectable to a first computer and second computer of the respective first and second imaging equipment for operating the table movement means in coordination with the production of images thereby.

In accordance with yet another facet of the invention, an object support system for supporting an object during the production of diagnostic images by a diagnostic imaging apparatus is provided. The object support system includes a table having an object support side for supporting the object thereon, a base for supporting the table above a floor and a means for moving the base relative to the floor. The object support system also includes at least one of a table movement means, disposed between the table and the base, for allowing movement of the table in a direction generally parallel with the longitudinal axis of the table and relative to the base and a table height adjustment means for adjusting the height of the table relative to the floor. The object support system includes a computer for controlling the table movement means and the means for adjusting. A linking means selectively connects the computer into communication with the diagnostic imaging apparatus. A data entry means is provided for entering examination specific data into the object handling computer. The computer controls the at least one of the table movement means and the means for adjusting as a function of position data stored in the diagnostic imaging apparatus and available to the object support system computer.

In accordance with a more limited aspect of the invention, the table is comprised of different materials at opposite ends of a longitudinal axis of said table.

In accordance with still another aspect of the invention, the computer includes data relating to the production of diagnostic images, said image production data being available to the diagnostic imaging apparatus when the computer is linked to the imaging apparatus. The imaging apparatus uses the image production data in the production of diagnostic images thereby.

In accordance with another facet of the invention, a method of diagnostic imaging an object on a first and second diagnostic imaging apparatus is provided. In the method, an object is disposed on an movable object handling system having a table disposed over a base. The object handling system is docked relative to the imaging space of the first diagnostic imaging apparatus. The first diagnostic imaging apparatus produces diagnostic images of the object in the associated imaging space. The object handling system is undocked from the first imaging apparatus and moved to the second imaging apparatus where it is docked relative to the imaging space of the second imaging apparatus. The second imaging apparatus produces diagnostic images of said object in the associated imaging space.

In accordance with a more limited aspect of the method, the top is extended relative to the base and into one of the first imaging space and second imaging space for the production of diagnostic images thereby. The top is retracted out of the one of the first imaging space and second imaging space after the production of diagnostic images by the respective one of the first imaging apparatus and the second imaging apparatus.

In accordance with yet another more limited aspect of the method, data is entered into a data storage means disposed on the object handling system prior to producing diagnostic images of said object with one of the first imaging apparatus and the second imaging apparatus. The data storage means is connected to the one of the first imaging apparatus and second imaging apparatus prior to producing diagnostic images therewith and the data is associated with the images of said object produced by the one of the first and second imaging apparatus.

An advantage of the present invention is that a patient can be disposed on an object handling equipment and imaged on more than one diagnostic imaging apparatus by moving the object handling equipment, with patient disposed thereon, between the various types of imaging apparatus.

Still another advantage of the present invention is that it includes an on-board computer for storing object identification data that is useable by the various imaging apparatus. The on-board computer being selectively linkable with the various imaging apparatus such that the object identification data is available to the linked imaging apparatus.

Yet another advantage of the present invention is that it includes a height adjustment means for adjusting the height of the table relative to the floor and/or a table movement means for moving the table relative to the base. The height adjustment means and table movement means are connected to the on-board computer which modifies the operation of the height adjustment means and table movement means as a function of the type of imaging apparatus the on-board computer is linked with.

Still other advantages will become apparent upon reading and understanding the following detailed description.

BRIEF DESCRIPTION OF THE DRAWINGS

FIG. 2 is an end view of the object handling system of FIG. 1 when viewed from the end of the object handling system opposite the Computed Tomographic Scanner.

FIG. 3 is a side view of the object handling system, in accordance with the present invention, disposed under an x-ray source.

FIG. 4 is a close up view of the base end of the object handling system of FIG. 1 disposed adjacent the Computed Tomographic Scanner of FIG. 1.

FIG. 5 is a perspective view of a diagnostic imaging room in which an object handling system of the present invention is disposed between a Computed Tomographic Scanner and an Angio system and oriented for use with the Computed Tomographic Scanner.

DETAILED DESCRIPTION OF THE PREFERRED EMBODIMENT

Figure 1:
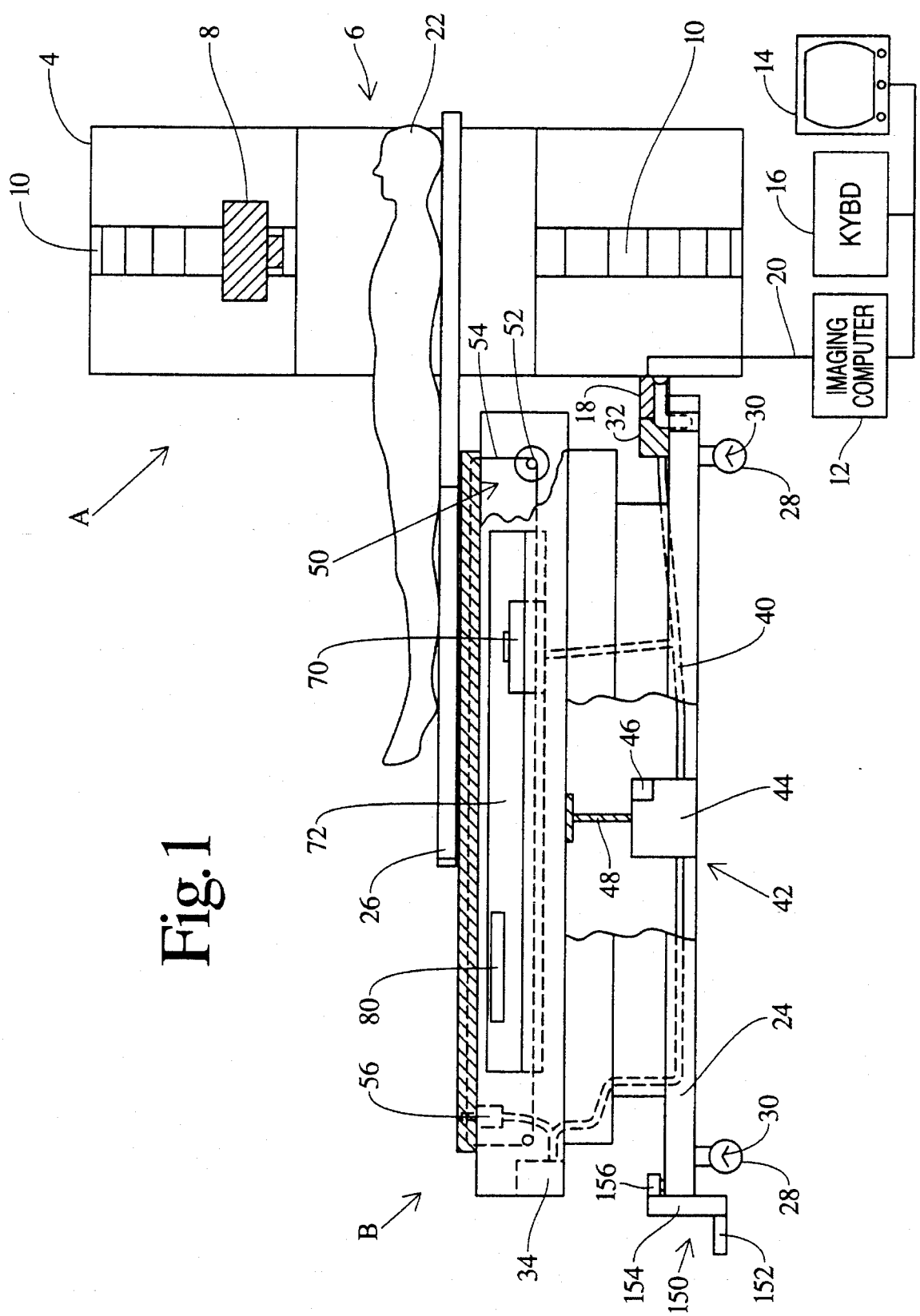
FIG. 1 is a side view of an object handling system, in accordance with the present invention, disposed in operative relation to a cross section of a Computed Tomographic Scanner.

With reference to FIG. 1, a medical diagnostic imaging apparatus of a first type A, such as a CT, is comprised of a gantry 4 which forms an imaging space 6 for receiving patients during imaging operations. A CT is shown for convenience, however, therapy systems as well as other modalities of diagnostic imaging apparatus, such as MRI, X-ray, Nuclear Medicine Cameras, and the like, and imaging spaces formed thereby, either alone or in conjunction with other equipment (not shown), are contemplated. The gantry supports an x-ray tube 8 for rotation about the imaging space 6. A plurality of x-ray detectors 10 are disposed for receiving radiation from the x-ray tube that has traversed the imaging space. Each x-ray detector produces an electrical signal that is proportional to the amount of radiation received by each detector. The imaging apparatus includes an imaging computer 12 for managing the operation of the apparatus, receiving the electrical signals from the x-ray detectors, processing the electrical signals into image data for presentation on a first display means 14 and the like. A first data entry means 16, such as a keyboard, is connected to the imaging computer for facilitating operator input of commands and data to the imaging computer. The imaging apparatus also includes a first connector 18 which will be described in greater detail below. The first connector and imaging computer are electrically connected to each other by a system cable 20. The operation of such imaging apparatus is within the knowledge of one skilled in the art.

With reference to FIG. 2 and continuing reference to FIG. 1, a multi-modality object handling system B supports an object 22 to be imaged in the imaging space 6. The object handling system can be used with two or more different modalities of imaging equipment or with two or more different imaging equipment of the same imaging modality. By way of example and not of limitation, the object handling system may be useable with an MRI apparatus and a CT apparatus or it may be useable with two or more different models of CT. The object handling system is comprised of a base 24 and a table 26 of longitudinal extent disposed on top of the base for supporting the object. Wheels 28 are disposed between the base and the floor for allowing the table and base to be moved relative to the floor. Each wheel includes a locking means 30 for selectively locking the wheel against rolling.

The object handling system includes a second connector 32, disposed on the base 24, and an object handling computer 34. A second data entry means 36, such as a keyboard, and a second display means 38 are connected to the object handling computer to facilitate entry of various data into the object handling computer. The second connector 32 is electrically connected to the object handling computer 34 by a harness 40. The first connector 18 and second connector 32 are designed to mate. Mating the first connector 18 and the second connector 32 facilitates electrical connection, and consequently a data communication path, between the imaging computer 12 and the object handling computer 34.

A height adjustment means 42, for adjusting the height of the table relative to the floor, is disposed between the base and the table. The height adjustment means is comprised of a drive means 44, a position sensor 46 and a gear arrangement 48. The drive means 44 position sensor 46 mechanically connected to the gear arrangement 48 and are electrically connected to the object handling computer 34 via harness 40. The object handling computer monitors the position sensor 46 and controls the drive means 44 and such that gear arrangement adjusts the height of the table to a desired height. Alteratively, the gear arrangement 48 is manually adjusted using suitable mechanical means such as a manually adjustable scissor jack or hydraulic jack.

The object handling system further includes a table movement means 50 that allows the table to be moved in a direction along the longitudinal axis of the table and relative to the base. The table movement means may also provide for manual movement of the table transverse to the longitudinal axis of the table and relative to the base. The table movement means includes a motor 52 and drive belt 54. The motor is connected to the drive belt which in-turn is connected to the table. The motor has an internal decoder/resolver for determining the position of the table relative to the base. The motor and decoder/resolver are electrically connected to object handling computer 34 by harness 40. The motor 52 and drive belt 54 provide for automated movement of the table relative to the base. Specifically, the object handling computer 34 energizes the motor which in-turn pulls the drive belt thereby moving the table into or out of the imaging space in coordination with position information provided to said computer by the encoder/resolver. Alternatively, if the motor 52 is not energized, the table is manually moveable relative to the base.

The object handling system includes a table lock 56 disposed on the base 24 and electrically connected to the object handling computer 34 by harness 40 for locking the table relative to the base under the control of the object handling computer. Alternatively, the table lock 56 is manually engageable or disengageable.

With reference to FIG. 3, and continuing reference to FIG. 1-2, the base 24 has a pair of apertures 58 disposed one on either side of second connector 32. The gantry 4 has a pair of hooks 60 connected to the lower portion of the gantry and disposed one on either side of the first connector 14. The apertures 58 and hooks 60 are disposed on the base and gantry respectively such that when the first connector 18 and second connector 32 are mated the ends of the hooks 60 opposite the gantry are disposable in the apertures 58. Disposing the hooks 60 in the apertures 58 secures the base relative to the gantry 4 and consequently the imaging space 6. Alternate means for securing the base to the gantry, such as a pin and collar arrangement, are also contemplated.

In operation, the table lock 56 is engaged to secure the table to the base. The object 22 is disposed on the table, generally in a room other than the room in which the first imaging apparatus is located. Object identification data and imaging data are entered into the object handling computer 34 via the second data entry means 36. The object identification data is comprised of data unique to the object being imaged. Imaging data is comprised of data related to the control of various elements of the diagnostic imaging apparatus used to produce diagnostic images of the object, e.g., the power output by an x-ray tube, step or spiral scanning by a CT, a pulse sequence to be used by an MRI apparatus, and the like. The object handling system B and object are moved to the imaging apparatus and the base 24 is positioned such that the first connector 18 and second connector 32 mate thereby creating the data communication path between the imaging computer 12 and the object handling computer 34. The hooks 60 are disposed in their respective apertures 58 thereby securing the base 24 relative to the imaging space 6. The height adjusting means 42 is adjusted as required for the height of the imaging space 6. The wheel locking means 30 are engaged to lock the wheels 28 against rotation or pivoting. The table lock 56 is disengaged such that the table movement means 50 can selectively introduce the table into the imaging space 6 in coordination with the imaging operation.

The data communication path makes the object identification data and the imaging data available to the imaging computer 12 for use in producing diagnostic images by the associated imaging apparatus. Specifically, to produce a diagnostic image, the imaging computer 12 controls the various elements of the diagnostic imaging apparatus in accordance with at least one of instructions input to the imaging computer 12 through the first data entry means 16 and the imaging data stored in the object handling computer. The imaging computer 12 associates the object identification data with the images of the object produced by the imaging apparatus such that there is a correlation between the object and the produced images.

The imaging computer 12 and object handling computer 34 also communicate to coordinate the operation of the object handling system B with the operation of the imaging equipment. Specifically, the imaging computer includes information about the associated imaging equipment such as the modality of imaging equipment, the manufacturer, positioning data of the table relative to the imaging space of the imaging equipment, and the like. This imaging equipment information is available to the object handling computer when the first and second connectors are mated. The object handling computer 34 adjusts the table movement means 50 and/or the height adjustment means 42 as a function of the imaging equipment information such that the operation of the object handling system B is coordinated with the operation of the imaging equipment in the production of diagnostic images. For example, if a first imaging apparatus signals the object handling computer to advance the table a first distance, the object handling computer interprets the signal in light of the imaging equipment information from the first imaging computer and issues appropriate signals to the table movement means 50 to advanced the table accordingly. Similarly, a signal from a second imaging apparatus to advance the table the first distance is interpreted by the object handling computer in light of the imaging equipment information from the second imaging computer and the object handling computer issues appropriate signals to the table movement means 50 to advanced the table accordingly. In this manner, the table movement means 50 and the height adjustment means 42 are adjusted in accordance with the imaging equipment to which the object handling system is mated.

When imaging at the first imaging apparatus is complete, the hooks 60 are removed from their respective apertures, the first connector 18 and second connector 32 are separated and the object handling system B is moved to the second imaging apparatus. At the second imaging apparatus the first connector 18 of the second imaging apparatus and the second connector 32 are mated and the hooks 60 are disposed in their respective apertures 58. Like the above example, the object identification data and the imaging data are available to the imaging computer 12 of the second imaging apparatus for use in the production of diagnostic images thereby. Similarly, the object handling computer 34 and the imaging computer 12 of the second imaging apparatus coordinate the table movement means 50 and the height adjustment means 42 with the production of diagnostic images by the second imaging apparatus.

The operation of the object handling system with X-ray imaging equipment will be described in greater detail next with reference to FIG. 4 and continuing reference to FIGS. 1–3. In FIG. 4, an x-ray source 70, such as an x-ray tube, is disposed on the object handling system in an aperture 72 disposed opposite the object side of the table. The x-ray source 70 is movable in the aperture so that the x-ray source may be positioned therealong. The x-ray source is connected to harness 40 for control by the object handling computer 34 and/or the imaging computer 12. Energizing the x-ray tube causes it to direct a radiation beam 74 upward along a radiation beam path 76. An image intensifier 78 is disposed in the beam path 76 above the table and is connected to the imaging computer 12. Mating the first connector 18 to the second connector 32 connects the object handling computer 34 to the imaging computer 12 thereby providing the imaging computer with access to object identification data and imaging data stored in the object handling computer. The intensity and duration of the radiation beam 74 is controlled in accordance with instructions input to the imaging computer through the first data entry means 16 and/or the imaging data stored in the object handling computer. The image intensifier 78 converts radiographic information contained in the radiation beam 74 into a viewable image. The imaging computer 12 coordinates the acquisition of the viewable image from the image intensifier 78 with the production of radiation from the x-ray source 70. The imaging computer 12 also associates the object identification data with the viewable images. The imaging computer 12 transmits the viewable images and object identification data to the first display means 14 for viewing, to a storage device for storage thereof, and the like. Additionally, an film carrier 80 may be disposed in the aperture 72. The film carrier supports x-ray film for exposure by another radiation source 82 disposed above the table.

In an alternate embodiment, an x-ray sensitive electronic array (not shown) is connected to the object handling computer 34 and/or the imaging computer 12 and replaces the image intensifier 78 or the film carrier 80.

In most imaging applications, there is one diagnostic imaging system per room. The choice to have one diagnostic imaging system per room is dictated, in part, by a desire to maximize the availability of the imaging system. There is, however, growing interest in applications wherein imaging equipment of two different types, i.e., an Angio type x-ray system and a CT system, are disposed in the same room to facilitate correlative studies of a patient. One such application includes precisely positioning a catheter in a patient using an Angio system and then introducing a pharmaceutical into the patient via the catheter while the patient is being imaged by a CT system. In this case, it is desirable to move the patient between the respective imaging equipment as quickly and efficiently as possible so as to not disturb the catheter position and to minimize patient discomfort.

Figure 6:
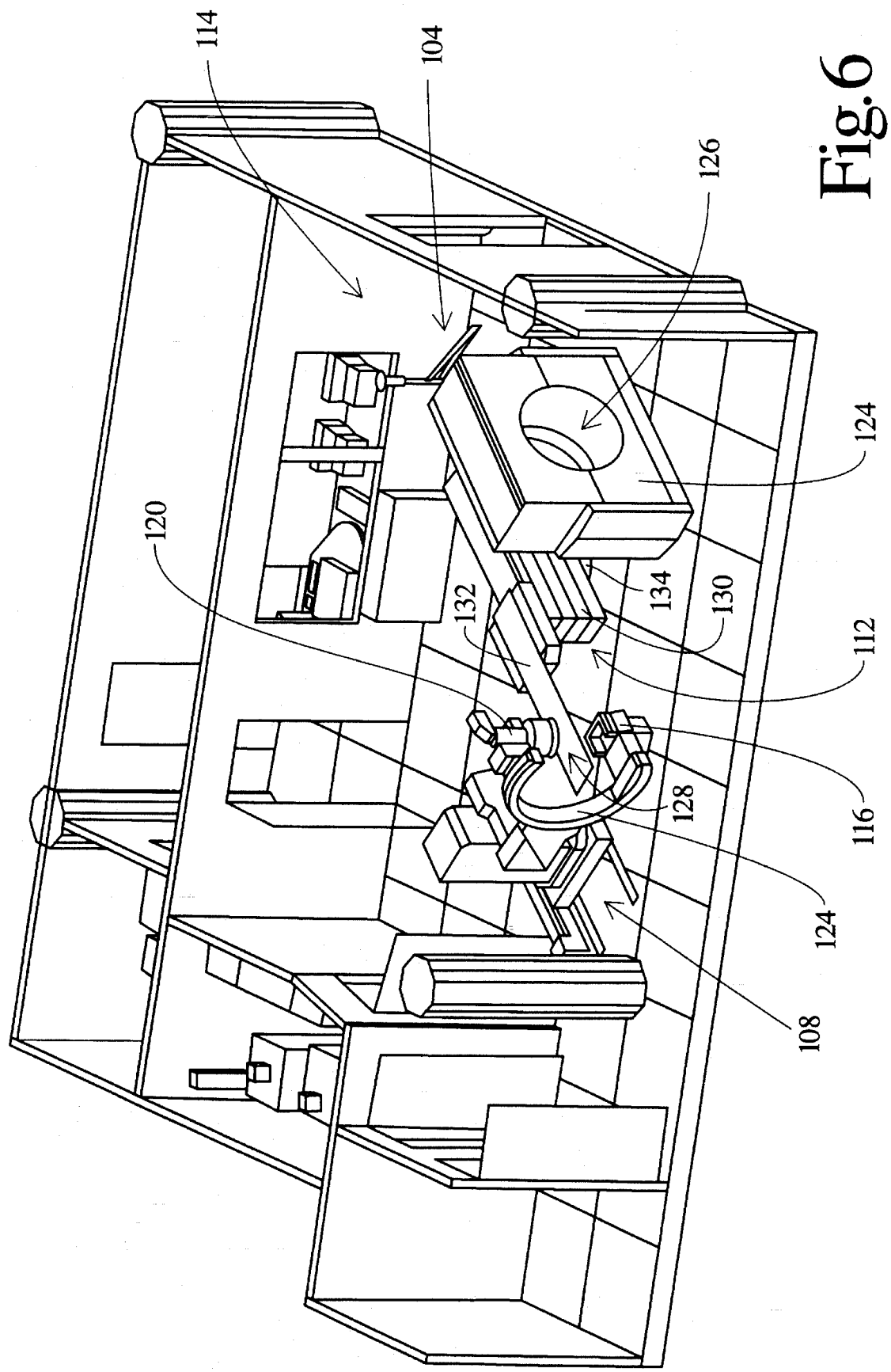
FIG. 6 is a perspective view of the diagnostic imaging room as viewed from a side of the room opposite the view illustrated in FIG. 5 with the object handling system oriented for use with the Angio system.

With reference to FIGS. 5–6 and continuing reference to FIGS. 1–4, a CT system 104, an Angio system 108 and an object handling system 112 are disposed in room 114. The Angio system 108 comprises an x-ray source 116 and an image intensifier 120 disposed on opposite sides of a C-arm 124 such that radiation from the x-ray source is directed at the receiving face of the image intensifier. The x-ray source 116 and image intensifier 120 form an imaging space 128 in which a patient is disposed during imaging. The CT system 104 has a gantry 124 that forms an imaging space 126. In FIG. 5, the base 130 of the object handling system 112 is oriented such that the table 132 is extendable into the CT imaging space 126. When the imaging operation on the CT system 104 is complete, the table, with patient thereon, is withdrawn from the CT imaging space 126. The orientation of the object handling system, with patient disposed thereon, is changed such that the table is disposable into the imaging space 128 of the Angio system. This change in orientation is accomplished by moving the object handling system on the wheels 28 as set forth above in conjunction with the discussion of FIG. 1. Alternatively, the base may be disposed on pivot 134 that allows the table to be pivoted between the CT system and the Angio system. The operation of the table movement means 50 and/or the height adjustment means 42 is selectively controllable as a function of the orientation of the object handling system to the Angio system or CT system.

The object handling system 112 is used in two different manners depending on whether the handling system is used with the CT system or the Angio system. Specifically, when used in conjunction with the CT system, it is desirable for the table movement means 50 to move, or index, the table into the imaging space of the CT system in coordination with the production of diagnostic images. In contrast, when used with the Angio system, it is desirable for the table to "float" on the base such that an attending physician can manually move the table thereby controlling the position of the patient in the imaging space of the Angio system. To facilitate the floating top, the table movement means 50 is not energized when the table is used with the Angio system. Alternatively, a means for selectively engaging the table movement means 50 to the table 132 may be provided.

The above object handling system applications are described in conjunction with diagnostic imaging environments. However, the above described object handling system also finds application as a collapsible object handling system for use in a vehicle such as a truck or an ambulance. In this discussion the object handling system is used to support a patient in an ambulance, however, it is to be appreciated that use of the object handling system in other vehicles or with objects, other than patients, is contemplated. When used in an ambulance, the height adjustment means 42 lowers the table, as illustrated in FIG. 4, so that the object handling system B, with a patient disposed thereon, can be loaded into and transported in the ambulance. During transportation, at least one of patient identification data and imaging data are entered into the object handling computer 34 via the second data entry means 36. When the ambulance arrives at a hospital, clinic or other such facility, the object handling system B and patient are unloaded from the ambulance and the height adjustment means 42 raises the object handling system to a convenient height for movement thereof into the facility. The facility has a first connector 18 connected to a hospital computer, used to record information about patients such as admission time, insurance carrier, treatment, and the like. The first connector 18 is not rigidly attached to a housing but rather is at the end of a flexible harness 20 to allow the first connector 14 and second connector 28 to be joined without having to orient the object handling system in a specific direction. Once the first connector 18 and second connector 32 are joined, the object handling computer 34 transfers patient identification data to the hospital computer thereby speeding up the patient admittance cycle. When the patient is ready to be imaged, the object handling system B is docked to the imaging equipment and at least one of the patient identification data and imaging data are transferred from the object handling computer 34 to the imaging computer 12 for use in the production of images by the imaging equipment associated with the imaging computer. An advantage of using the object handling system B in this manner is that during transportation, patient identification data and/or imaging data is entered into the object handling computer 34 thereby enhancing the efficiency of admission to the hospital.

In an alternate embodiment of the present invention, the object handling system B, and specifically the table, is preferentially comprised of materials at opposite ends of the table. Specifically, tables used with MR imagers are commonly made from a fiberglass composite that includes strands of fiberglass held together by an epoxy resin. Similarly, tables used with x-ray or CT imagers are commonly made from a carbon composite that includes carbon and epoxy. Because the present invention finds application with more than one imaging modality, it is desirable that the table 22 be useable with more than one imaging modality. Accordingly, the table is comprised of different materials at opposite ends of the longitudinal axis of the table. For example, one end of the table 26 is comprised of carbon composite while the other end is comprised of fiberglass composite. In use, the patient is oriented on the table 26 such that a portion of the patient to be imaged is positioned at the end of the table comprised of material preferable for use with a specific imaging modality to be used on the portion of the patient.

An alterative to the first connector 18 and second connector 32 to link the imaging computer 12 and object handling computer 34 includes an r.f. or an optical communication link. Specifically, the first connector and second connector are replaced by r.f. or optical transceivers. Using an r.f. or optical communication transceiver avoids the need to physically connect the first connector 18 and second connector 32. Moreover, the r.f transceiver may be useful in transferring patient identification data and/or Imaging data from the ambulance to the hospital, clinic or other such facility prior to arriving at the hospital, thereby further enhancing admission of the patient at the facility.

Lastly, with reference to FIGS. 1 and 2, when the table extends from the base, (as shown in FIG. 1) the center of gravity of the object handling system shifts in the direction of the extension. To secure the object handling system to the floor when the table is extended, a damp means 150 is secured between the base of the object handling system and the floor. Specifically, the clamp means is comprised of a first horizontal plate 152 secured to the floor, a vertical plate 154 connected to and extending upwards from the first plate and a second horizontal plate 156 attached to the vertical plate and extending over and engaging a portion of the base. It is to be appreciated that different types of passive or active clamping means to secure the base to the floor are anticipated. Moreover, a clamping means to secure the connector end of the base to the floor, to minimize shifting of the base when the first connector 18 and second connector 32 are joined, is also anticipated.

The above invention has been described with reference to the preferred embodiments. Obvious modifications and combinations will occur to others upon reading and understanding the preceding description. It is intended that the invention be construed as including all such modifications, combination and alterations insofar as they come within the scope of the appended claims of the equivalents thereof.

Having described the preferred embodiment the invention is now claimed to be:

1. A medical diagnostic imaging means for producing medical diagnostic images of an object, said means comprising:
   a diagnostic imaging equipment of a first type for producing a first diagnostic image of the object;
   a diagnostic imaging equipment of a second type for producing a second diagnostic image of the object, said first and second imaging equipment having respective first and second imaging computers for controlling the production of diagnostic images thereby, said first and second imaging equipment forming respective first and second imaging spaces; and
   an object handling system for use in supporting said object during examination comprising:
   a table for supporting the object during examination;
   a base for supporting said table above a floor;
   a computer for storing data relating to the identification of the object under examination; and
   a means for selectively linking the object handling system computer to one of the first and second imaging equipment, said linking means providing a data communication path between the object handling system computer and the computer of the selected one of the first and second imaging equipment such that said identification data is available to the computer of the selected one of the first and second imaging equipment for use in the production of diagnostic images.

2. The medical diagnostic imaging means as set forth in claim 1 further including a means for entering the identification data into the object handling system computer.

3. The medical diagnostic imaging means as set forth in claim 1 further including a base movement means disposed between the base and the floor for allowing movement of the base and table from the selected one of the first and second imaging equipment to the other imaging equipment.

4. The medical diagnostic imaging means as set forth in claim 3 wherein the linking means includes a means for securing the base relative to at least one of the first and second imaging spaces.

5. The medical diagnostic imaging means as set forth in claim 3 further including one or more of (i) a means for disposing said table into the imaging space of the selected one of the first and second imaging systems and (ii) a means for adjusting the height of the table from the floor.

6. The medical diagnostic imaging means as set forth in claim 5 wherein the object handling system further includes a table lock for locking the table in a selected position relative to the base.

7. The medical diagnostic imaging means as set forth in claim 5 wherein at least one of the first and second imaging computers store positioning data relating to the relative position of the table and the respective imaging space necessary for object examination, said data communication path allowing said positioning data to be available to the object handling system computer for use during the production of diagnostic images, wherein the one or more of said means for disposing and means for adjusting is controllable by the object handling computer and responsive to the positioning data.

8. The medical diagnostic imaging means as set forth in claim 1 wherein the linking means is comprised of a first connector connected to the computer of the selected one of the first and second imaging systems and a second connector connected to the object handling computer, said first and second connectors designed to mate together.

9. The medical diagnostic imaging means as set forth in claim 1 wherein the linking means comprises one of an r.f. and an optical communications link, said optical link operating in one of the infrared, visual and ultraviolet range.

10. The medical diagnostic imaging means as set forth in claim 1 wherein the object handling system further includes at least one of (i) a film carrier, (ii) an x-ray sensitive array and (iii) an image intensifier.

11. A medical diagnostic system comprising:
   a first diagnostic imaging equipment for producing a first diagnostic image of an object;
   a second diagnostic imaging equipment for producing a second diagnostic image of the object, said first and second imaging equipment having respective first and second imaging computers for controlling the production of diagnostic images thereby, said first and second imaging equipment forming respective first and second imaging spaces; and a means for sustaining an object during examination by the first and second diagnostic imaging equipment, said sustaining means comprising:

a table for supporting said object;

a means for supporting the table relative to the floor, said support means being moveable between said first and second imaging equipment such that said table is selectively disposable in the first and second imaging spaces;

table movement means disposed between the table and the support means for moving the table relative to the support means; and a computer connected to the table movement means, said sustaining means computer being selectively connectable to the first and second computers, said connection providing a data communications path therebetween.

12. The medical diagnostic system of claim 11 wherein the sustaining means computer contains data that is utilizable by at least one of said first and second computers in the production of diagnostic images and which is available to the selected one of said first and second computers through the data communications path.

13. The medical diagnostic system of claim 11 wherein at least one of said first and second computers contains data that is utilizable by said sustaining means computer and which is available to said sustaining means computer through the data communications path, whereby the sustaining means computer causes the sustaining means to operate in coordination with the production of diagnostic images.

14. An object support system for supporting an object during the production of diagnostic images by a diagnostic imaging apparatus, said support system comprising:

a table of longitudinal extent having an object support side for supporting the object thereon, said table having a longitudinal axis extending along said longitudinal extent;

a base for supporting the table above a floor;

a means for moving the base relative to the floor;

one or more of (i) a table movement means, disposed between the table and the base, for allowing movement of the table in a direction generally parallel with the longitudinal axis of the table and relative to the base and (ii) a means for adjusting the height of the table relative to the floor;

a computer for controlling the one or more of the table movement means and the means for adjusting;

a linking means for selectively connecting the computer into communication with the diagnostic imaging apparatus; and a data entry means connected with the object handling computer for entering examination specific data into the object handling computer, said diagnostic imaging apparatus including positioning data relating to the relative position of the table to the diagnostic imaging apparatus, said data being available to the computer for controlling the one or more of the table movement means and the means for adjusting as a function of the relative position data.

15. The object support system as set forth in claim 14 further including at least one of (i) a film carrier, (ii) an x-ray sensitive array and (iii) an image intensifier disposed opposite the object support side of the table and connected to the linking means.

16. The object support system as set forth in claim 14 wherein the table is comprised of different materials at opposite ends of the longitudinal axis of said table.

17. The object support system as set forth in claim 14 wherein the linking means is one of an r.f. and an optical communications link between the object handling system computer and the outboard computer.

18. The object support system as set forth in claim 14 wherein the computer includes data relating to the production of diagnostic images, said image production data being available to the diagnostic imaging apparatus for use in the production of diagnostic images.

19. A method of producing images using a first and second diagnostic imaging apparatus, said first and second imaging apparatus forming respective first and second imaging spaces, the method comprising:

disposing an object on a movable object handling system having a table disposed over a base;

docking the object handling system relative to the first imaging space;

producing diagnostic images of said object with the first imaging apparatus;

undocking the object handling system;

moving the object handling system, with the object disposed thereon, to the second imaging apparatus;

docking the object handling system relative to the second imaging space;

producing diagnostic images of said object with said second imaging apparatus;

entering data into a data storage means disposed on the object handling system prior to producing diagnostic images of said object with one of the first imaging apparatus and the second imaging apparatus; and connecting the data storage means to one of the first imaging apparatus and second imaging apparatus prior to producing diagnostic images therewith, whereby the selected one of said imaging apparatus associates the data with the images of said object produced by said selected one of said first and second imaging apparatus.

20. A medical diagnostic system comprising:

a first diagnostic imaging equipment for producing a first diagnostic image of an object;

a second diagnostic imaging equipment for producing a second diagnostic image of the object, said first and second imaging equipment forming respective first and second imaging spaces;

means for controlling the production of diagnostic images by said first and second imaging equipment; and a means for sustaining an object during examination by the first and second diagnostic imaging equipment, said sustaining means comprising:

a table for supporting said object;

a means for supporting the table relative to the floor, said support means being moveable between said first and second imaging equipment such that said table is selectively disposable in the first and second imaging spaces;

table movement means disposed between the table and the support means for moving the table relative to the support means; and a computer connected to the table movement means and to said means for controlling, said sustaining means computer containing data that is utilizable by the means for controlling.

21. A patient handling system for use in supporting a patient during medical imaging by at least one imaging apparatus having an imaging space and an imaging computer, said system comprising:

a table for supporting the patient;

a base for supporting said table above a floor;

a computer for storing data relating to the patient;

a means for entering data into the computer; and a means for selectively linking the handling system computer to said imaging computer, said linking means providing a data communication path between said handling system computer and the imaging computer such that the data is available for use by the imaging computer during medical imaging.

22. The patient handing system of claim 21 further comprising a base movement means disposed between the base and the floor, the movement means allowing movement of the base between at least a first and second imaging apparatus.

23. The patient handling system of claim 22 further comprising one or more of a (i) means for disposing said table into the imaging space of the selected imaging apparatus; and (ii) means for adjusting the height of the table from the floor.

24. The patient handling system of claim 23 wherein at least one of the first and second imaging equipment stores positioning data relating to the relative position of the table and the respective imaging space necessary for examination of the patient, said data communications path permitting the transfer of said positioning data from the selected imaging equipment to the handling system computer, whereby the one or more of said means for disposing and means for adjusting is controllable by the handling system computer and responsive to the positioning data.

* * * * *